(12) United States Patent
Kim et al.

(10) Patent No.: US 6,503,396 B2
(45) Date of Patent: Jan. 7, 2003

(54) METHOD AND APPARATUS FOR PREPARING TAXOL USING SUPERCRITICAL FLUID FROM SOURCE MATERIALS

(75) Inventors: Jin Woong Kim, Seoul (KR); Young Hae Choi, Seoul (KR); Ki Pung Yoo, Seoul (KR); Min Jeong Noh, Daejon (KR); Joo Hee Han, Daejon (KR)

(73) Assignee: Hanwha Chemical Corporation, Seoul (KR)

( * ) Notice: Subject to any disclaimer, the term of this patent is extended or adjusted under 35 U.S.C. 154(b) by 0 days.

(21) Appl. No.: 09/792,273

(22) Filed: Feb. 23, 2001

(65) Prior Publication Data

US 2002/0000410 A1 Jan. 3, 2002

(30) Foreign Application Priority Data

Feb. 25, 2000 (KR) .............................. 00-9255

(51) Int. Cl.[7] .......................... B01D 11/02; A61K 35/78
(52) U.S. Cl. .................... 210/634; 210/198.2; 210/511; 210/656; 424/770; 549/510; 549/511
(58) Field of Search ................................ 210/634, 635, 210/638, 639, 656, 198.2, 511, 194, 195.1, 805, 259, 774, 806; 422/70; 436/161; 549/510, 511; 424/769, 770, 776; 546/348

(56) References Cited

U.S. PATENT DOCUMENTS

| | | | | |
|---|---|---|---|---|
| 4,683,063 A | * | 7/1987 | Rice | ............................ 210/634 |
| 4,898,673 A | * | 2/1990 | Rice et al. | .................... 210/634 |
| 5,019,504 A | | 5/1991 | Christen et al. | |
| 5,319,112 A | * | 6/1994 | Kingston et al. | ........... 549/510 |
| 5,440,055 A | * | 8/1995 | Castor | ........................ 549/510 |
| 5,480,639 A | * | 1/1996 | Elsholy et al. | ............... 549/510 |
| 5,654,448 A | * | 8/1997 | Pandey et al. | ............... 549/510 |
| 5,750,709 A | * | 5/1998 | Castor | |
| 5,854,064 A | * | 12/1998 | Castor et al. | |
| 6,136,989 A | * | 10/2000 | Foo et al. | .................... 439/510 |
| 6,291,241 B1 | * | 9/2001 | Castor et al. | |

FOREIGN PATENT DOCUMENTS

| | | |
|---|---|---|
| CN | 1192382 | 9/1998 |
| KR | 1994-7829 | 11/1995 |
| KR | 1995-703845 | 2/1996 |
| KR | 1994-36099 | 7/1996 |
| KR | 1996-55302 | 2/1997 |
| KR | 1996-19486 | 3/1998 |
| WO | WO 92/07842 | 5/1992 |
| WO | WO 94/20486 | 9/1994 |

OTHER PUBLICATIONS

Chun et al., "Supercritical Fluid Extraction of Taxol and Baccatin III from Needles of *Taxus cuspidata*," *Biotechnology Techniques*, 1994, 8(8):547–550.

Fang et al., "Separation and Concentration of Crude Taxol Sample Using Supercritical Fluid $CO_2$ Extraction and Recrystallization–Adsorption," *Yunnan Daxue Xuebao, Ziran Kexueban*, 1999, 21(4):288–290 (English abstract provided).

Jennings et al., "Supercritical Extraction of Taxol from the Bark of *Taxus brevifolia*," *J. Supercritical Fluids*, 1992, 5:1–6.

(List continued on next page.)

*Primary Examiner*—Joseph W. Drodge
(74) *Attorney, Agent, or Firm*—Fish & Richardson, P.C., P.A.

(57) ABSTRACT

Methods for isolating taxol and derivatives thereof with high purity are described. The methods include a supercritical fluid and a cosolvent extraction step, a liquid—liquid separation step, and a column chromatography step. An apparatus for isolating Taxol and derivatives thereof that allows the method steps to be performed online also is described.

30 Claims, 8 Drawing Sheets

OTHER PUBLICATIONS

Vandana and Teja, "Supercritical Extraction of Paclitaxel Using $CO_2$ and $CO_2$–Ethanol Mixtures," *ACS Symp. Ser.*, 1995, 608:429–443.

Bicchi et al., "Off–Line Supercritical Fluid Extraction and Capillary Gas Chromatography of Pyrrolizidine Alkaloids in Senecio Species," *J. Nat. Prod.*, 1991, 54(4):941–945.

Chiu and Chang, *The Illustrated Medicinal Plants of Taiwan*, 1992, vol. 3, SMC Publishing Inc., Taipei, Taiwan, p. 32.

Elisabeth et al., "Infrared and Nuclear Magnetic Resonance Spectrometry of Caffeine in Roasted Coffee Beans after Separation by Preparative Supercritical Fluid Chromatography," *Anal. Sci.*, 1991, 7:427–431.

Janicot et al., "Extraction of major alkaloids from poppy straw with near–critical mixtures of carbon dioxide and polar modifiers," *J. Chromatogr.*, 1990, 505:247–256.

Kim et al., "Effect of Plant Matrix and Fluid Ethanol Concentration on Supercritical Fluid Extraction Efficiency of Schisandrin Derivatives," *J. Chromatographic Sci.*, 1999, 37:457–461.

Kingston et al., "The Chemistry of Taxol, A Clinically Useful Anticancer Agent," *J. Nat. Prod.*, 1990, 53:1–12.

Luque de Castro et al., *Analytical–Scale Supercritical Fluid Extractor*, 1994, Springer–Verlag, Berlin, pp. 188–189.

Ndiomu and Simpson, "Some Applications of Supercritical Fluid Extraction," *Anal. Chim. Acta.*, 1988, 213:237–243.

Powell et al., "Alkaloids of *Cephalotaxus wilsoniana*," *Phytochemistry*, 1972, 11:3317–3320.

Rowinsky et al., "Taxol: A Novel Investigational Antimicrotubule Agent," *J. Nat. Cancer Inst.*, 1990, 82(15):1247–1259.

Schaeffer et al., "Supercritical Fluid Isolation of Monocrotaline from *Crotalaria spectabilis* Using Ion–Exchange Resins," *Ind. Eng. Chem. Res.*, 1989, 28(7):1017–1020.

Schiff et al., "Promotion of microtubule assembly *in vitro* by taxol," *Nature*, 1979, 277:665–667.

Spencer and Faulds, "Paclitaxel—A Review of its Pharmacodynamic and Pharmacokinetic Properties and Therapeutic Potential in the Treatment of Cancer," *Drugs*, 1994, 48(5):794–847.

Sugiyama et al., "New Double–Stage Separation Analysis Method—Directly Coupled Laboratory–Scale Supercritical Fluid Extraction–Supercritical Fluid Chromatography, Monitored with a Multiwavelength Ultraviolet Detector," *J. Chromatogr.*, 1985, 332:107–116.

Tena et al., "Supercritical Fluid Extraction of Natural Antioxidants from Rosemary: Comparison with Liquid Solvent Sonication," *Anal. Chem.*, 1997, 69(3):521–526.

Wani et al., "Plant Antitumor Agents. VI. The Isolation and Structure of Taxol, a Novel Antileukemic and Antitumor Agent from *Taxus brevifolia*," *J. Am. Chem. Soc.*, 1971, 93(9):2325–2327.

Witherup et al., "High Performance Liquid Chromatographic Separation of Taxol and Related Compounds from *Taxus brevifolia*," *J. Liquid Chromatogr.*, 1989, 12(11):2117–2132.

* cited by examiner

METHOD AND APPARATUS FOR PREPARING TAXOL USING SUPERCRITICAL FLUID FROM SOURCE MATERIALS

FIELD OF THE INVENTION

The present invention relates to methods and an apparatus for extracting and purifying taxol and derivatives thereof from source materials containing the same. In particular, the methods and apparatus can be used in separating taxol and its derivatives from needles and other parts of yew trees.

BACKGROUND OF THE INVENTION

Numerous compounds that exhibit therapeutic activity in the treatment of diseases have been isolated and identified in organic solvent extracts from plant material, microorganisms and marine organisms. Some of the compounds that have been demonstrated to have a particularly good physiological activity have been used as chemotherapeutic or anti-HIV agents. However, investigation into the therapeutic utility of these compounds has been hindered by the extreme abundance of natural sources to be screened and the inefficiencies of conventional extraction techniques.

Examples of such useful compounds include plant alkaloid derived from *Vinca rosea* and its semisynthetics vinblastine and vincristine, and taxol (NSC 125973), a diterpene alkaloid plant product derived from the pacific yew, *Taxus brevifolia*.

Taxol

Taxol is one of a class of drugs inhibiting mitosis of eukaryotic organisms. It promotes polymerization of tubulin and stabilizes the structure of intracellular microtubules to produce an anti-cancer effect (see, Schiff, P. B. et al., *Nature* 277, 665–667 (1979)).

In the 1960's, taxol was discovered as a result of a plant screening program organized by the US National Cancer Institute (NCI). After cytotoxic activity was first found in a crude extract from the bark of the Pacific yew tree, *Taxus brevifolia*, the active compound was isolated in 1966. It was named taxol in 1967, and its molecular structure was characterized by Wani et al. in 1971 (Wani, M. C. et al., *J. Am. Chem. Soc.*, 93: 2325, 1971). Horwitzi et al. (1979) elucidated its active mechanism (Horwitz, F. B., et al., *Nature*, 1979, 277, 665 and Eric K. Rowinsky et al., *J. National Can. Inst.*, 82, 11247 (1990)). According to NCI's reports, the response rate to taxol of ovarian cancer, breast cancer or lung cancer patients, all who have exhibited no response to conventional anti-cancer drugs, were 30%, 50% and 20%, respectively (David, G., et al., *J. Nat. Prod.*, 53, 1 (1990)).

Marketing approval of taxol as an anti-cancer drug started from 1992, when the US Food and Drug Agency (FDA) and the HPB (Canada) approved the use of taxol for the treatment of ovarian cancer. In 1994, the use of taxol for the treatment of breast cancer and Kaposi's sarcoma was approved by the FDA. Subsequently, the FDA approved taxol for treating non-small-cell lung cancer (NSCLC) in 1997 and expanded the use of taxol to early breast cancer in 1999. In addition, taxol has been reported in studies to exhibit excellent effects on other types of cancer (Spencer, C. M. and Faulds, D., *Drug.* 48, 794–847 (1994)).

Conventional Preparation of Taxol

The conventional purification method is performed in four major steps. First, the acetone:hexane mixture from the extraction process is chromatographed on Florisil columns in a 70/30 hexane:acetone mixture to separate the taxol containing fractions. The taxol fractions are then concentrated to dryness. This step may be repeated as many as nine times. Second, taxol concentrates are crystallized from a methanol:water mixture and then recrystallized from an acetone:hexane mixture yielding 85 to 95% pure taxol. Third, the taxol is chromatographed on silica gel packed with either 2.5% isopropanol or 2.5% n-butanol in methylene chloride to yield approximately 98% pure taxol. Fourth, the taxol is dissolved in acetone, the solution filtered, and taxol recrystallized from an acetone:hexane mixture. This organic phase extraction and chromatographic purification process yields 99% pure taxol, which is about 0.014% of the milled bark (*J. Liquid Chromatography*, 12(11): 2117–2132 (1989); WO 92/07842).

The production of taxol by this technique is encumbered by the following: (i) time consuming extraction and purification procedures; (ii) long residence times in a harsh environment; and (iii) low overall yields. Also, the bark of *T. brevifolia* is usually obtained from mature trees (100 to 200 years old). The bark is thus in limited supply.

Many studies have been conducted to overcome such problems and to provide alternate routes for obtaining taxol. Some of the alternate routes include total chemical synthesis and cell culturing synthesis. Several total chemical synthesis methods were reported in 1994. However, these methods were difficult to commercialize due to their complicacy. This problem originated from the fact that taxol has several asymmetric carbon atoms and a complex structure. The production of taxol through cell culturing has also undergone some difficulties in commercializing because of the slow rate of cell growth and the easy browning of cells (U.S. Pat. No. 5,019,504, issued May 28, 1991).

Yew trees can be classified into the following genera: Amentotaxus, Austrotaxus, Cephalotaxus, Pseudotaxus, Taxus, Torreya, etc. Among them, Taxus genus includes, for examples, *T. brevifolia, T. baccata, T. media, T. wallichiana, T. Canadensis, T. cuspidate*, etc, which are generally considered to be suitable sources for extraction of taxol and its derivatives.

Yew trees, such as *T. cuspidate*, which have a high taxol content in their needles, have been planted plentifully with regard to landscape and are easy to cultivate in farm fields. However, the trees have high levels of wax and non-polar components, which makes the separation of taxol therefrom difficult. The total amount of taxol in organic solvent extracts from the bark was 25%, but the content of impurities was very high in the range of 35–42%. In order to easily separate taxol from *T. cuspidate*, one must first develop selective removal techniques of materials such as waxes and chlorophyll.

The term "impurities" herein refers to all components of extracts from plants with the exception of taxol and its derivatives.

The use of supercritical fluid in the extraction of taxol has been proposed for improved extraction. The term "supercritical fluid" refers to a fluid that is above its critical pressure and above its critical temperature. A supercritical fluid has both the gaseous property of being able to penetrate anything and the liquid property of being able to dissolve materials into their components. In addition, it offers the advantage of being able to change density to a great extent in a continuous manner and by adjustment of the system pressure and temperature. This advantage is connected to simple control of its dissolving capability. As such, use of supercritical fluids is offered as a substitute for organic solvents in the fields of food industry and medical supplies.

Furthermore, supercritical fluids do not extract chlorophyll (M. T. Tena et. al. *Analytical Chemistry, Vol.* 69, No.

3, 521 (1997)). Particularly, supercritical carbon dioxide is advantageous in extracting desired ingredients from plants without chlorophyll extraction.

KR patent application Nos.1994-7829, 1994-36099, 1995-703845, 1996-19486 and 1996-0055302 describe methods for extracting taxol from plants with supercritical carbon dioxide.

In particular, KR patent application No.1994-7829 discloses a method and an apparatus for continuously separating and purifying taxol with high purity wherein supercritical fluid extraction is accomplished in a countercurrent manner. Cosolvents are also employed in the invention.

KR patent application No.1994-36099 discloses the use of n-hexane in removing non-polar substances prior to supercritical carbon dioxide extraction. Namely, it suggests a combining method of organic solvent extraction with supercritical carbon dioxide extraction.

KR patent application No.1995-703845 is a method for extracting taxol from the needles of ornamental yew comprising the steps: (a) dewaxing the needles by subjecting said needles to supercritical fluid, (b) subjecting said dewaxed needles to supercritical fluid and cosolvents and (c) separating taxol through column chromatography. However, this method has some problems, such as a risk of taxol loss during the dewaxing step and the incomplete extracting capability of the cosolvents employed.

KR patent application Nos. 1996-55302 and 1996-19486 disclose extraction methods similar to the methods indicated above.

Consequently, conventional supercritical fluid extraction techniques are not optimal for taxol extraction.

Taxol is linked to cell walls in plants through a weak chemical bond. Depending on the properties of solvents used, taxol can be partially extracted from plants. Supercritical carbon dioxide makes plants swell, which allows for the desired substances to be easily extracted, whereas its polarity makes the extraction of high polar and chemically linked substances (e.g., taxol) difficult (M. D. Luque de Castro et. al. *Analytical Supercritical Fluid Extraction*, Springer-Verlag, Berlin, p. 188 (1994), Y. Kim et. al. *J. Chromatographic Science*, Vol. 37, 457 (1999)).

Also, organic solvents cannot easily penetrate plants and are limited in their ability to extract taxol.

SUMMARY OF THE INVENTION

The present invention provides a novel method for preparing taxol and derivatives thereof, comprising a supercritical fluid extraction step, an organic solvent extraction step, and a chromatographic step (e.g., a multi-column chromatographic step). The invention overcomes limits in conventional supercritical fluid extraction by employing cosolvents optimized for taxol extraction in the first step.

In one aspect, the invention features a method for isolating Taxol or derivatives thereof from a source material. The method includes (a) extracting the source material with a supercritical fluid (e.g., supercritical carbon dioxide) and a cosolvent to obtain an extract; (b) liquid—liquid separating the extract with an organic solvent to obtain a solvent layer; and c) isolating Taxol or the derivatives thereof from the solvent layer by column chromatography. The steps can be conducted in a continuous or non-continuous manner. The ratio of the supercritical fluid to the cosolvent can be between 75:25 and 85:15.

A cosolvent serves to release taxol and its derivatives from the matrix of source materials. Preferably, the cosolvent has a —OH group in its chemical structure. For example, the cosolvent can be a mixture of water and at least one alcohol (e.g., methanol or ethanol). Examples demonstrate cosolvents that include water and alcohol, such as methanol and ethanol. At least one of the cosolvents can be used simultaneously. Preferably, a mixture of water and alcohol is used. A volume ratio of water to alcohol is preferably from 30:70 to 5:95 and more preferably 20:80. Further, additional solvents, such as acetic acid and triethylamine, can be added to the cosolvents, for example, to 1%(v/v). Acetic acid acidifies the supercritical fluid and cosolvents, and triethylamine bacifies the supercritical fluid and cosolvents. Cosolvent selection criteria are further described in Example 1 below. The volumetric ratio of water to at least one alcohol can be between 30:70 and 5:95 (e.g., 20:80).

In step (a) in accordance with the present invention, preferable conditions of the supercritical fluid comprise a temperature of 60 to 100° C. and a pressure of 300 to 400 bars. More preferably, the temperature is in the range of 75 to 85° C. and the pressure is in the range of 330 to 370 bars. Most preferably, about 80° C. and about 350 bars are selected. A flow rate of supercritical fluids is preferably between 30 and 50 kg/hr. The supercritical fluid extracting step also can be performed at a temperature of 75 to 85° C., a pressure of 330 to 370 bars, and a flow rate of 30–50 kg/hr of the supercritical fluid.

In step (b), preferable examples of the organic solvent include n-hexane. N-hexane can combine with the cosolvent (preferably, alcohol) from step (a) and then participate in liquid—liquid separation together with alcohol. N-hexane is preferably fed in an amount similar to that of the cosolvent. Namely, a volume ratio of n-hexane to the cosolvent (preferably alcohol) becomes 1:1. Step (b) may be repeated one to three times. The extracting and liquid—liquid separating steps can be performed continuously or non-continuously.

Step (c) can include multi-column chromatographic procedures. Each column chromatographic procedure can be performed continuously or non-continuously.

Examples of resins that can be used include silica gel, RP-18, Sephadex, and pentafluorophenyl resin. Each of the multiple columns includes a column resin. For example, silica gel, RP-18, and Sephadex column resins can be used. A column including a pentafluorophenyl resin can be used as the final column when multiple columns are used.

In silica gel column chromatography, silica gel may be used in an amount of 10 times the extract weight and a stepwise gradient system of chloroform:methanol (e.g., 1:0→0:1 v/v) can be used as an eluant. Preferably, fractions containing taxol and its derivatives can be obtained. Alternatively or additionally, silica gel may be used in an amount of 33 times the weight of extracts applied to the column, and elution may be performed with dichloromethane:methanol (e.g., 85:15 v/v).

The amount of the RP-18 resin can be 10 times the extract weight applied to the column, and methanol can be used as eluant. Fractions containing Baccatin III can be eluted from the RP-18 resin.

The amount of the Sephadex resin can be 65 times the extract weight applied to the column, and methanol can be used as eluant. Cephalomannine can be eluted from the Sephadex resin.

In Sephadex column chromatography, Sephadex resin may be used in an amount of 65 times the extract weight and methanol can be employed as an eluant. Preferably, fractions containing cephalomannine may be obtained by the elution.

In one embodiment of the invention, a final column used in step (c) may include a pentafluorophenyl resin. The amount of the pentafluorophenyl resin can be 133 times the extract weight applied to the column. An acetonitrile:water gradient system can be used as eluant. Acetonitrile content can be changed from 60% to 90% during the course of the chromatography (e.g., changed from 60% to 80% during the first 40 minutes and then a further increase to 90% during an additional 10 minutes).

The method further can include recrystallizing the isolated taxol and derivatives thereof (e.g., to increase purity of the product). A solution of water:methanol (1:1 v/v) can be used.

The source material to which the method of the invention can be applied is plant material containing taxol or its derivatives. The most suitable plants are species of Taxus, such as *T. brevifolia, T. baccata, T. media, T. wallichiana* and *T. canadensis, T. cuspidate*, but are not limited thereto. Among the Taxus species, *T. cuspidate* is particularly preferred. Also, taxol and its derivatives can be extracted from the whole plant or from separated parts such as wood, stems, bark, roots, leaves (needles), seeds or mixtures thereof. The material can be dried. Preferably, the bark or the needles are used.

The invention also features an apparatus for isolating Taxol and derivatives thereof from source materials. The apparatus includes a reservoir for supercritical fluid, an extractor into which the source material can be fed, a separating vessel that separates the supercritical fluid from the extract mixtures, a liquid—liquid separator, and at least one column chromatography, all being placed online (e.g., all within a single production line). The apparatus further can include at least one separating vessel, which separates the supercritical fluid from the extract mixtures in a continuous form. The apparatus can allow the recovery and recycling of a full amount of solvents used in the liquid—liquid separator with the exception of solvents transferred into column chromatography.

In one preferable embodiment of the invention, the apparatus comprises at least one separating vessel, which separates the supercritical fluid from the extract mixture, in a continuous form.

In another preferable embodiment of the invention, the apparatus allows the recovery and recycling of a full amount of solvents used in the liquid—liquid separator with the exception of solvents transferred into column chromatography. One preferable embodiment of such apparatus is illustrated in FIG. 1, which exemplifies the use of a n-hexane and alcohol mixture in the liquid—liquid separator.

The following advantageous effects were obtained by the present invention:

The invention can provide a simple method for extracting and separating taxol and its derivatives by combining a supercritical fluid extraction with an organic solvent separation and avoid the complicated extraction procedure of conventional taxol extraction methods.

The invention can provide certain optimal cosolvents for taxol extraction in view of both, (i) the capability of dissolving taxol and its derivatives, and (ii) the ability of releasing taxol and its derivatives from the matrix of source materials. As a result, the invention provides an improved taxol extraction in terms of efficiency.

The invention also provides special conditions between the supercritical fluid and cosolvents for improved taxol extraction. Further, the invention illustrates a cellulose paper-taxol model showing the cosolvents' mechanism of action during the extraction. The inventors deduced from the model that water may be useful as a cosolvent and supported the conclusion by providing experimental results to show that a cosolvent mixture of water and alcohol increases the extraction yield (see Examples hereinafter).

The method of the invention increased the yield of taxol to an amount 2 times that of conventional methanol extractions. An "extraction selectivity" that is related to the absolute amount of taxol contained in extracts was demonstrated to increase 5.5 times as compared with the methanol extractions.

The invention also provides a chromatographic assembly comprising 5 columns, which allows a simple purification in comparison with conventional methods. Also, all of the resins used are confirmed to be recyclable.

BRIEF DESCRIPTION OF THE DRAWINGS

FIG. 7($a$) is a HPLC chromatogram obtained from methanol extraction and FIG. 7($b$) is a HPLC chromatogram obtained from supercritical fluid extraction.

FIG. 8($a$) shows the results from RP-18 resin column chromatography. FIG. 8($b$) shows HPLC analysis of taxol finally obtained.

Figure 1:
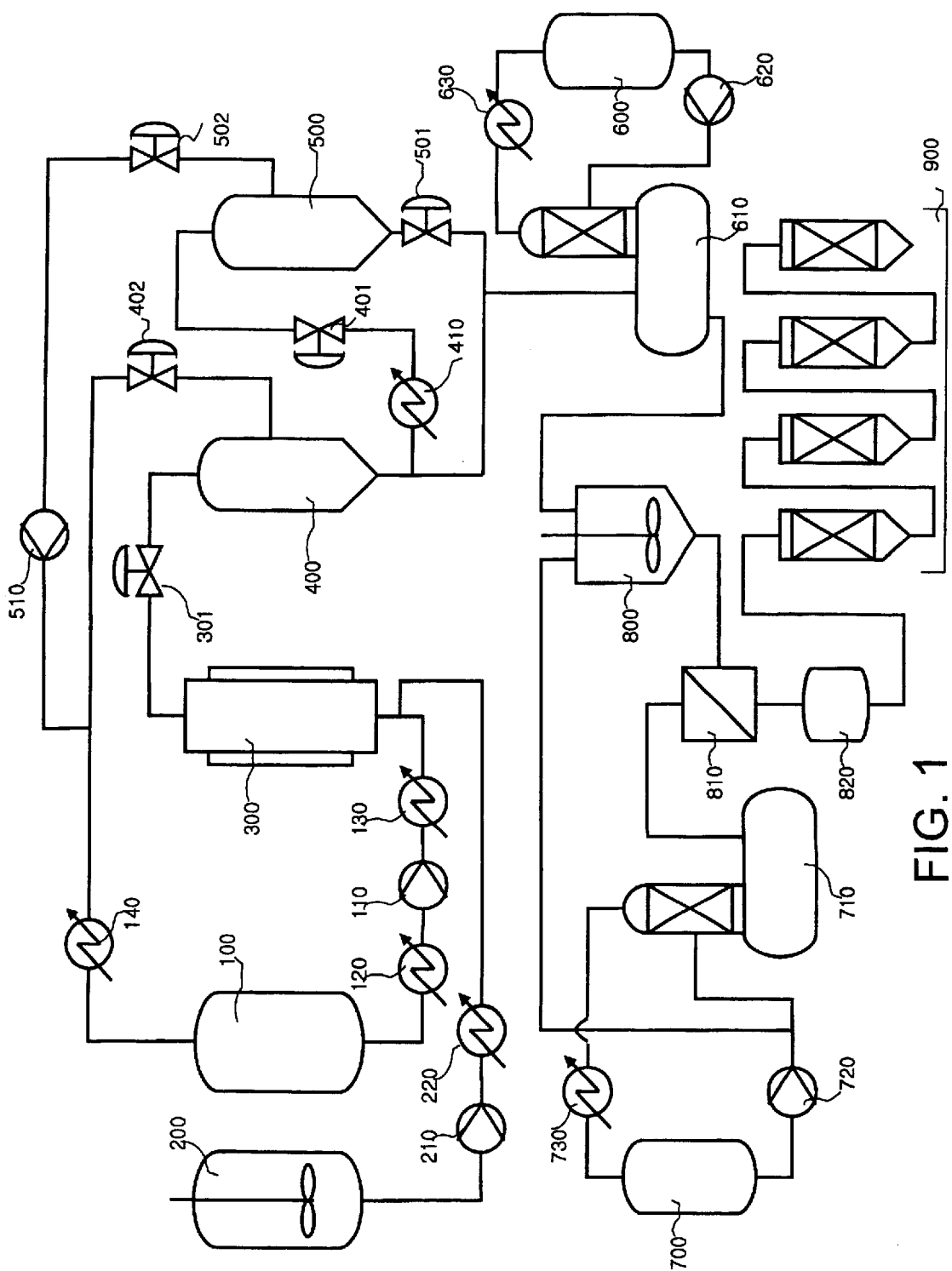
FIG. 1 is a schematic view of an apparatus for preparing taxol and its derivatives according to the present invention. The apparatus allows execution of a supercritical fluid extraction step, an organic solvent separation step and a column chromatographic step, all online.

Each number in the drawings refer to the following devices:

| | |
|---|---|
| 10: carbon dioxide cylinder | 11: carbon dioxide booster pump, |
| 12: $CO_2$ feeding on/off valve | 13: $CO_2$/cosolvent mixer, |
| 14: major solvent feeding on/off valve | 20: cosolvent bottle |
| 21: cosolvent booster pump | 22: cosolvent feeding on/off valve |
| 30: manifold | 31: vent valve |
| 40: isotherm extractor | 41: extraction cell |
| 50: isothermal restrictor box | 60: collection box |
| 51: restrictor | 100: carbon dioxide reservoir |
| 61: collection vial | 120: heat exchanger for cooling $CO_2$ |
| 110: carbon dioxide booster pump | 140: heat exchanger for liquefying $CO_2$ |
| 130: heat exchanger for heating $CO_2$ | 210: cosolvent booster pump |
| 200: cosolvent mixing reservoir | 300: extractor |
| 220: heat exchanger for cosolvent | 400: first separating vessel |
| 301: back pressure regulator | 402: back pressure regulator |
| 401: liquid phase control valve | 500: second separating vessel |
| 410: heat exchanger for heating/cooling | 502: back pressure regulator |
| 501: liquid phase control valve | 600: alcohol reservoir |
| 510: booster for pressing $CO_2$ | 620: alcohol circulation pump |
| 610: alcohol evaporator | 700: hexane reservoir |
| 630: heat exchanger for cooling | 720: hexane circulation pump |
| 710: hexane evaporator | 800: mixer of alcohol with hexane |
| 730: heat exchanger for cooling | 820: concentrator |
| 810: liquid-liquid separator | |
| 900: multi-column chromatography assembly | |

DETAILED DESCRIPTION OF THE INVENTION

The method for preparing taxol and its derivatives according to the invention will be more specifically illustrated below, with reference to the attached drawings.

Figure 2:
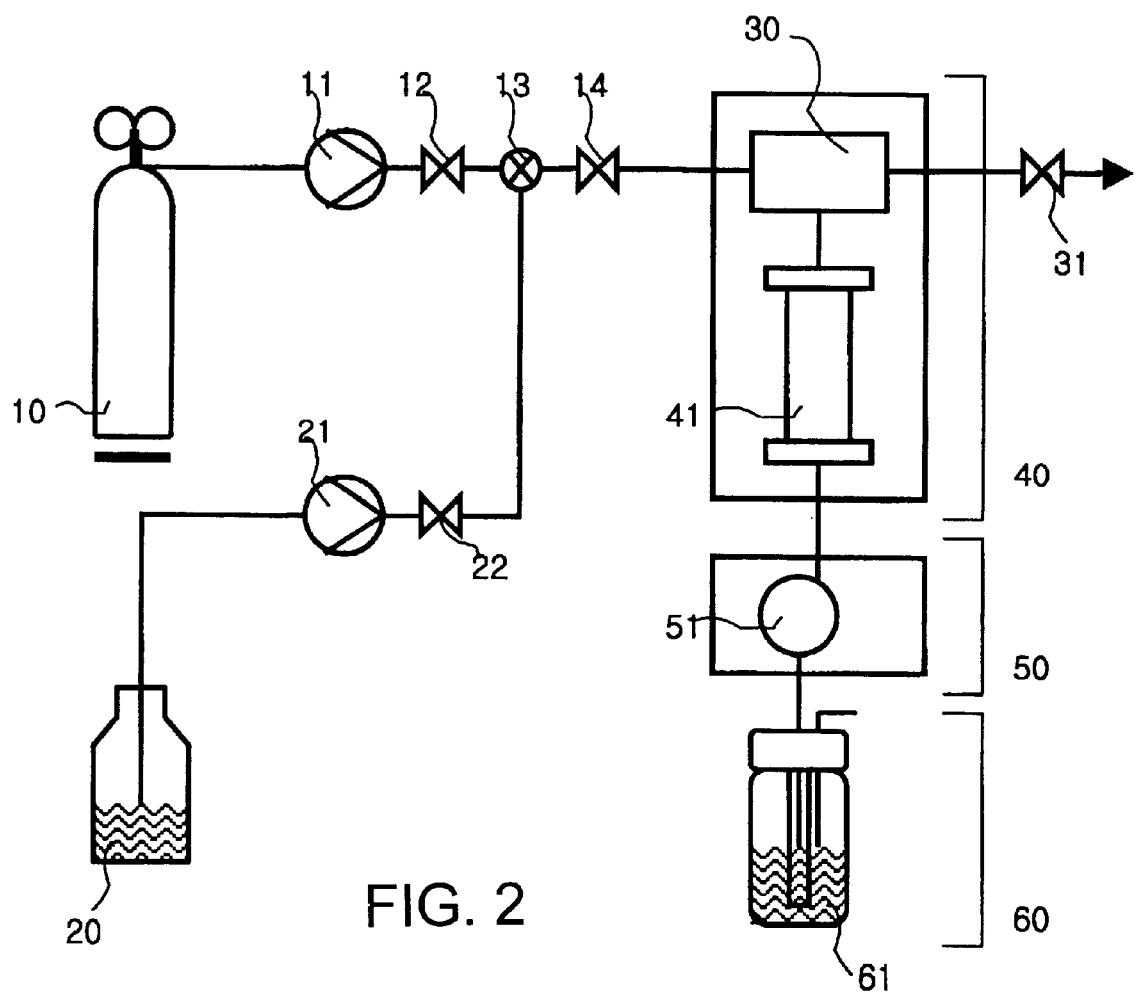
FIG. 2 is a schematic view of a supercritical fluid extraction apparatus of the present invention.

Embodiments of the method of the invention may be performed with the supercritical fluid extraction apparatus depicted in FIGS. 1 and 2. For large scale source materials, the apparatus in FIG. 1 may be used in step (a). The apparatus in FIG. 2 can be used for processing a small amount of source materials.

Even though the use of supercritical $CO_2$ as a supercritical fluid is illustrated in both apparatuses of FIGS. 1 and 2, it is recognized and understood that this is only for the convenience of description and the supercritical fluid of the invention is not limited to $CO_2$.

Referring to FIG. 2, the method is described in detail. One example of the apparatus depicted in FIG. 2 is Model 703 Supercritical Fluid Extractor (DIONEX, USA). This apparatus was used herein and comprises a $CO_2$ booster, a cosolvent mixer and booster, an isothermal extractor, an isothermal restrictor box and a collection box.

The apparatus may be operated in the following manner:

Extraction cell 41 is filled with a dried and ground source material, such as dried and ground needles of the yew tree. Carbon dioxide is transferred from $CO_2$ cylinder 10 to $CO_2$ booster pump 11 and then pressurized therein. Liquid $CO_2$ can be used in order to facilitate the operation of the booster pump. Cosolvent bottle 20 is previously filled with one cosolvent or a mixture containing two solvents in a specific ratio. The cosolvent is pressurized to a desired pressure with cosolvent booster pomp 22. Upon completion of the pressurization of the $CO_2$ and the cosolvent to the desired pressure, valves 12 and 22 are switched on so that said $CO_2$ and cosolvent can flow into mixer 13. Valves 12 and 22 control the movement of said $CO_2$ and cosolvent, respectively, and mixer 13 mixes the $CO_2$ with the cosolvent. After mixing, the $CO_2$ and cosolvent are transferred from mixer 13 to extraction cell 41 via valve 14 and manifold 30. Valve 14 serves as an on/off switch for controlling the movement of the $CO_2$ and cosolvent. Before the $CO_2$ and cosolvent are introduced, extraction cell 41 and manifold 30 are set up and maintained at a constant temperature by virtue of isotherm extractor 40. The $CO_2$ and cosolvent remain at a constant temperature and pressure during the passage through manifold 30. In extractor 41, subsequently, the extraction of the source materials is started upon the entering of the $CO_2$ and cosolvent. During the extraction, a flow rate of the $CO_2$ and cosolvent remains constant by means of booster pumps 11 and 21, while a highest value of the flow rate is controlled by restrictor 51. After extracting in extraction cell 41, the resulting extracts containing the $CO_2$ and cosolvent are transferred to collection box 60 via restrictor 51. At this time, the extracts undergo a pressure fall that may cause a drop of temperature. Such a temperature drop can lead to clogging of restrictor 51. However, isothermal restrictor box 50 prevents the temperature drop and clogging of restrictor 51.

The extracts passing restrictor 51 undergo a pressure fall by which the $CO_2$ is vaporized and vented as gas. The remaining cosolvent and extracts are collected into collection vial 61.

The cosolvent and extracts in collection vial 61 is subjected to vacuum evaporation to remove all of the solvent constituents. The extracts containing taxol are obtained, dissolved in a small amount of methanol, and applied into HPLC analysis for quantitative assay. Before this, the yew extracts in methanol may be filtered through a filter, such as $C_{18}$ sep-pak of Waters (Milford, Mass., USA) in order to enhance the accuracy in the quantitative assay.

The HPLC system used in the experiment by the inventors was HP-1090M, available from Hewlett Packard (USA), which incorporates a UV detector for quantitation of taxol at 228 nm and a Curosil PFP HPLC column (250×4.6 mm, 5 μm) settled with a Curosil PFP (30×4.6 mm, Phenomenex, Torrance, Calif., USA) guard column. The Curosil PFP HPLC column is used exclusively in taxol analysis. A mobile phase was used that included acetonitrile and water in a gradient mode, where a volume ratio of acetonitrile was increased from 25% early to 65% during the first 40 minutes and then to 80% during an additional 10 minutes.

Taxol and its derivatives utilized as a standard were obtained from Sigma-Aldrich (St. Louis, Mo., USA) and were semi-synthetic paclitaxel (non-cell-culture) (Taxol®), baccatin III, 10-deacetyl-baccatin III from Taxus baccata), 9-dihydro-13-acetylbaccatin III), and cephalomannine.

HPLC grade elutants used included methanol, chloroform, n-hexane, acetonitrile, and deionized water; all of which were obtained from J. T Baker (Philipsburg, N.J. USA). Reagent grade eluants such as methanol, chloroform and methylene chloride from DAI-JUNG Chemical Co. (Inchun, Korea) were also utilized.

In step (a), a preferable ratio of the $CO_2$ to cosolvent is in the range from 70:30 to 90:10. In cases where a mixture of alcohol and water as the cosolvent is used, alcohol comprises from minimum 50% to maximum 100% v/v. The alcohol involves in controlling a polarity of supercritical carbon dioxide and the water is responsible for breaking a weak chemical bond of taxol with plants.

For the treatment of a large scale of source materials, a supercritical $CO_2$ extraction apparatus in FIG. 1 may be used in the method according to the present invention.

The invention may be performed as described below with the apparatus in FIG. 1.

Step (a)

A basket filled with source materials is inserted into extractor 300. Liquid $CO_2$ contained in reservoir 100 is forced to flow toward heat exchanger 120. $CO_2$ in reservoir 100 exists as being liquid. Heat exchanger 120 cools $CO_2$ so that $CO_2$ can remain in liquid state. By virtue of this action of the heat exchanger 120, cavitation in $CO_2$ booster pump 110 can be avoided, although it may occur as a result of probable $CO_2$ vaporization. $CO_2$ is subsequently compressed by the booster pump and experiences phase transition to a supercritical fluid state by heat exchanger 130 for heating $CO_2$. In the first stage, feeding $CO_2$ into extractor 300 is continued until a pressure of $CO_2$ in extractor 300 becomes the same as the one in reservoir 100. The pressure of $CO_2$ in extractor 300 is also controlled by back pressure regulator 301. Upon completion of feeding $CO_2$ into extractor 300, $CO_2$ booster pump 110 begins to operate and elevates the pressure of $CO_2$. Simultaneously with this operation, a cosolvent (or cosolvents mixed in a certain ratio) in reservoir 200 is pressurized by booster pump 210. The pressure-elevated cosolvent is heated to a desired extraction temperature via heat exchanger 220, which serves as a heater of the cosolvent. The cosolvent then flows into extractor 300 along with supercritical $CO_2$. Extraction of the source materials is started after a temperature and pressure of extractor 300 is adjusted to a desired condition. Pressure in extractor 300 is controlled by back pressure regulator 301. When the supercritical fluid and cosolvent pass through extractor 300, their flow rates are regulated by booster pumps 110 and 210, respectively. The supercritical fluid and cosolvent emitted from extractor 300 would contain taxol and its derivatives extracted from the source materials, which then, are flowed into first separating vessel 400. First separating vessel 400 selectively vaporizes the supercritical fluid in the mixture of the fluid and cosolvent containing taxol and its derivatives. The $CO_2$ gas occurred is recovered to reservoir 100. Back pressure regulator 403 controls the pressure of $CO_2$ in the first separating vessel 400 to force the $CO_2$ gas to be sent to reservoir 100. During the recovery procedure, heat exchanger 140 converts $CO_2$ gas to liquid $CO_2$. In first separating vessel 400, the remaining $CO_2$ and the cosolvent in which taxol and its derivatives (i.e. extracts) are dissolved continue to be collected until they reach a certain level of liquid. The extracts are then forced to move into second separating vessel 500 via heat exchanger 410 and control valve 401. Control valve 401 regulates a level of liquid in first separating vessel 400. Heat exchanger 410 controls a temperature of the extracts to be constant, under which the cosolvent should not be vaporized.

Second separating vessel 500 completely vaporizes liquid $CO_2$ and the vaporized $CO_2$ is recovered to reservoir 100 for recycling. Back pressure regulator 502 controls the pressure of second separating vessel 500. The vaporized $CO_2$ emitted from the second separating vessel is pressurized by booster 510 and is then recovered to reservoir 100 along with the $CO_2$ from the first separating vessel via heat exchanger 140.

The level of liquid in the second separating vessel is controlled by control valve 501. If the extracts (i.e., the cosolvent and taxol extracts from the source materials) reach a certain level, the extracts above the level are collected into alcohol evaporator 610. This collection procedure is continuously performed.

After completion of the operation of step (a), all of the $CO_2$ remaining in extractor 300 and the first and second separating vessels 400 and 500 are recovered via back pressure regulator 502 and booster 510. After the completion of the supercritical fluid extraction step, the extracts remaining in alcohol reservoir 600, if any, is washed with alcohol fed by alcohol circulation pump 620 (not shown in the figure). The washes are collected to alcohol evaporator 610. After the washing operation, the remaining $CO_2$ in the separating vessels may be recovered as indicated above.

The apparatus features supercritical fluid (e.g., $CO_2$) recycling. The apparatus also features the employment of control valves for regulating a fluid level in separating vessels (e.g., 400 and 500). The valves serve to reduce the total level of contents in the separating vessels in cooperation with back pressure regulators (e.g., 402 and 502). The back pressure regulators can address the problem of limited capacity of the separating vessels.

Step (b)

This step begins with a mixture of the cosolvent and taxol-containing (or taxol derivative containing) extracts. It can be performed simultaneously with step (a). Step (b) functions to reduce the amount of the mixture to be subjected to step (c) by removing impurities from the mixture through liquid—liquid separation. Preferably, a mixture of n-hexane and alcohol may be used in the liquid—liquid separation. In the following, step (b) illustrates the use of a mixture of n-hexane and alcohol as an organic solvent.

The taxol-containing extracts transferred from step (a) to step (b) weigh 7%(w/w) of the source materials, and a taxol content in the extracts is 0.55% on the basis of the extracts weight.

The taxol content (%w/w) is related to "extraction selectivity." The term "extraction selectivity" indicates the absolute amount of taxol contained in the extracts that are obtained from a supercritical fluid (or organic solvent) extraction procedure. Supposing that the taxol content is the same in any source material and that the full amount of the taxol contained therein can be extracted, a larger amount of extracts corresponds to lower extraction selectivity. Also, a smaller amount of extracts means a higher extraction selectivity. Namely, the concept "extraction selectivity" is reversely correlated to the amount of impurities to be removed. When the extracts are subject to column chromatography, higher extraction selectivity is more advantageous in view of the economic use of resin. Higher extraction selectivity requires a smaller amount of resin used.

In order to enhance the extraction selectivity herein, step (b) was employed in this invention. Preferably, n-hexane is used along with alcohol for enhanced selectivity in this step.

In step (b), alcohol reservoir 600, alcohol evaporator 610, hexane reservoir 700, hexane evaporator 710, alcohol/hexane mixer 800, which includes a stirrer, liquid—liquid separator 810, which partitions extracts between an alcohol layer and a hexane layer, and concentrator 820. Concentrator 820 evaporates and concentrates a mixture of taxol-containing extracts and cosolvents.

Step (b) begins with the alcohol washes from washing alcohol reservoir 600, as mentioned above, in addition to said mixture. Alcohol evaporator 610 keeps above a temperature at which the cosolvent and alcohol can evaporate. Alcohol circulation pump 620 feeds liquid methanol into the evaporator to concentrate the solvents. The concentrates are transferred to alcohol/hexane mixer 800 in an amount of 1 to 5 1 Evaporated materials are emitted from the top of alcohol evaporator 610, condensed by heat exchanger 630 and flow into the alcohol reservoir. This procedure may be repeated one or two times to completely remove all of the extracted constituents that might still remain in evaporator 610 and the transfer pathway.

Subsequently, n-hexane is introduced into the extracts-containing alcohol in mixer 800 from hexane reservoir 700. The addition of n-hexane is carried out under control of hexane circulation pump 720 in the same amount as the flowing amount of the alcohol. Mixer 800 includes a stirrer, which promotes complete contact of the alcohol with n-hexane. As a result of the mixing, hexane soluble substances, such as waxes, move from the alcohol to the hexane. A total of the mixtures is then transferred to liquid—liquid separator 810 and partitioned between the alcohol and hexane layers. Hexane layer is subsequently transferred to hexane evaporator 710 while the alcohol layer is transferred to concentrator 820. Alternatively, alcohol in liquid—liquid separator 810 may be resent to mixer 800 to be subjected to hexane extraction, again (not shown in the figure). This procedure may be repeated one or two times.

The operation of hexane evaporator 710 is similar to that of alcohol evaporator 610 as described above. The remaining extracts after evaporation of hexane, if any, may be separately stored and, then, be applied to the isolation of the active ingredient.

The alcohol layer introduced to concentrator 820 undergoes alcohol evaporation. The vaporized alcohol is recovered to alcohol reservoir 600 (not shown in the figure). The concentrated alcohol layer will be transferred to step (c).

Step (b) features a simple and significant reduction of the amount of impurities in the extracts, which is subsequently subjected to column chromatographic step (c). Purification through column chromatographic techniques generally requires a large amount of solvents and long operation time. To avoid these problems, it is very important to reduce the amount of materials to be treated, as in the present invention.

Source materials undergo approximately 30% weight reduction during step (a), according to the invention. The amount of extracts obtained from step (a) is in the range of about 5 to 7% (w/w) of the source materials. At the same time, the taxol content increases from about 0.55% in the source materials to 0.82% in the extracts. About a 30% increase in extraction selectivity is also obtained.

The weight of the extracts obtained from a combination of steps (a) and (b) was about 3.5% to 5%(w/w) of the source materials. In cases where a conventional methanol extraction was carried out, the weight of extracts was generally about 15%(w/w) of the source materials. Consequently, the extraction selectivity of the invention is about 3 to 4.2 times higher than that of the conventional methanol extraction. Conventional organic solvent extractions, such as methanol extraction, present disadvantages in that there is a large amount of chlorophyll that is extracted from source materials by the organic solvent in addition to the desired substances. Therefore, if the hexane separation procedure of the present invention is applied to the conventional organic solvent extracts, a larger amount of hexane is needed. The present invention can avoid such problems by employing step (b).

Step (c)

Multi-column chromatography assembly 900 used in step (c) may comprise at least 2 types of column resin (e.g., 2, 3, 4 or more column resins). Preferably, step (c) can be divided into five purification procedures.

Preferably, resins used in each column may include silica gel G (Typ 60, TLC; Merck, Darmstadt, Germany), RP-18 (40–63 μm; Pharmacia Biotech, Uppsala, Sweden), Sephadex LH-20 (Pharmacia Biotech, Uppsala, Sweden), LiChroprep Si 60(40–63 μm Merck), LiChroprep RP-18(Merck) and Curosil-PFP (pentafluorphenyl): Phenomenex, Torrance, Calif., USA).

One preferable example of operation of step (c) is described as follows:

(1) First Purification: Silica Gel Column Chromatography

The resulting extracts from step (b) (preferably concentrated alcohol layer) are subjected to silica gel vacuum column chromatography. Silica gel may be used in an amount of 10 times the weight of the extracts (e.g., 10 g per 1 g extracts). A mobile phase used may be a chloroform:methanol (1:0→0:1 v/v) stepwise gradient system. The eluants may be fractionated in 5 Ml/g extracts. A mobile phase is changed from 100% chloroform to 100% methanol at Fraction 25. Taxol and its derivatives may be obtained in Fractions 45–52.

The term "stepwise gradient" indicates a gradient system in which one mobile phase is replaced with another mobile phase rapidly at a certain point, but not continuously. The stepwise gradient of chloroform:methanol (1:0→0:1(v/v)) refers to the replacement of 100% chloroform with 100% methanol as a mobile phase at a desired time point or upon passage of desired amount of eluants.

(2) Second Purification: RP-18 Column Chromatography

The resultant from the first purification above can be subjected to RP-18 column chromatography. The resin may be filled into the column in an amount of 10 times the weight of applied sample (e.g., 10 g per 1 g the applied sample). The mobile phase used is methanol. The resulting eluants may be fractionated in 2 Ml per 1 g of the applied sample. Taxol and its derivatives may be obtained in Fractions 7–10.

(3) Third Purification: Silica Gel Column Chromatography

LiChroprep Si 60 column filled with silica gel (40–63 μm) can be used here and the resin may be used in an amount of 33 times the weight of the applied sample (e.g., 33 g per 1 g the applied sample). Dichloromethane:methanol (85:15 v/v) solution can be used as a mobile phase. The resulting eluants may be fractionated in 33 Ml per 1 g of the applied sample. Taxol and its derivatives are detected in Fractions 7–10.

(4) Fourth Purification: Sephadex LH-20 Chromatography

Sephadex LH-20 is filled in an amount of 55 times the weight of the applied sample (e.g., 55 g per 1 g the applied sample). The resulting eluants are fractionated into 120 Ml methanol per 1 g of the added materials. Taxol and its derivatives are detected in Fractions 15–18.

(5) Fifth Purification: LH-20 Chromatography

A Curosil PFP column is used. The resin is used in an amount of 133 times the weight of the applied sample to be treated (e.g., 133 g per 1 g the applied sample). As a mobile phase, an acetonitrile-water gradient system where acetonitrile content is changed from 60% to 80% over a period of 40 minutes and then increased to 90% during an additional 10 minutes was used. Taxol and its derivatives can be obtained at a retention time of 14.0 minutes.

Example 9 below is performed in the same manner as that described above.

The present invention is further illustrated in the following examples, which is not intended to limit the scope of the invention in any way.

The present invention will be further described by the following examples, but these should not be construed as limiting the scope of the invention.

EXAMPLES

Source materials used in the examples and the comparative example were leaves, stems and roots of the *Taxus cuspidate*, which was taken from Medicinal Herb Garden, College of Pharmacy, Ilsan, Kyungi-Do, Korea.

The leaves, stems and roots of *Taxus cuspidate* were dried in a vacuum drying oven at 50° C. for 72 hrs. and then milled to the size of less than 0.7 mm with a miller. The resultant materials were used as source materials in the following examples and in the organic solvent extractions for the comparison of the effect of the invention. The materials were randomly selected for the exact comparison.

The taxol content of *Taxus cuspidate* is 2 to 4 times greater than that of the bark of *Taxus brevifolia*, the existing source materials of taxol, as one can see from the following comparative examples, which use a conventional organic solvent extraction.

COMPARATIVE EXAMPLE
The Amount of Taxol and its Derivatives Extracted using Organic Solvent This experiment was carried out to compare the present invention with conventional organic solvent extracting techniques in terms of an amount of taxol and its derivatives obtained.

The amount of taxol and its derivatives obtained from the leaves, stems and roots of *Taxus cuspidate* by methanol extraction were measured. The source materials used were the same as those in the examples given below. The source materials were added to methanol (100 ml), extracted under ultra-sonication for three hours, and then concentrated under a reduced pressure. The concentrated extracts were again dissolved in 1 ml of methanol. The resultant solutions were run to Sep-pak, which was previously washed with 10 ml of methanol, water and mixtures thereof (methanol:water= 55:45 v/v), respectively. The Sep-pak was eluted with 2 ml of methanol:water (55:45, v/v), 6 ml of methanol:water (80:20, v/v) and 2 ml of methanol. The combined 6 ml of methanol:water (80:20, v/v) fractions were concentrated under a reduced pressure, and then again dissolved in 1 ml of methanol. To facilitate high pressure liquid chromatography (HPLC) analysis, the dissolved fractions were subject to filtration through a PVDF membrane filter 13 mm in diameter and 0.45 μm in pore size (Lida Kenosha, Wis., USA). The filtrates were used as samples for the HPLC analysis to determine the contents of taxol and its derivatives in the samples. As a result, in *Taxus cuspidate*, 0.048% (0.48 mg/g) of taxol existed in leaves, 0.013% (0.13 mg/g) in stems and 0.019% (0.19 mg/g) in roots.

Example 1
The Effects of Cosolvent-types on Taxol Solubility in Supercritical Carbon Dioxide-cosolvents:

This example is directed to the selection of cosolvents capable of improving the solubility of taxol.

Taxol solubility was measured in supercritical $CO_2$ along with methanol, ethanol, water, or a combination of the cosolvent and 1%(v) of an auxiliary solvent such as acetic acid or triethylamine. Acetic acid acidifies the supercritical $CO_2$ and cosolvent, and triethylamine basifies the supercritical $CO_2$ and cosolvent. The results were shown in Table 1 below.

TABLE 1

The solubility of taxol in supercritical $CO_2$, cosolvent or both of them at 80° C., 350 bars (solubility = weight of taxol/volume of $CO_2$, μg/ml).

| Cosolvent | Volume ratio of cosolvent | | |
|---|---|---|---|
| | 1% | 5% | 10% |
| Methanol | 9.4 | 37.0 | 250.0 |
| Methanol + Triethanolamine (1% v/v) | 8.3 | 30.0 | 280.0 |
| Methanol + Acetic acid (1% v/v) | 9.5 | 38.0 | 250.0 |
| Ethanol | 4.9 | 32.0 | 130.0 |
| Ethanol + Triethanolamine (1% v/v) | 9.4 | 36.0 | 150.0 |
| Ethanol + Acetic acid (1% v/v) | 6.8 | 27.0 | 110.0 |
| Water | 6.1 | 4.0 | 2.9 |
| Water + Triethanolamine (1% v/v) | 15.0 | 10.0 | 8.7 |
| Water + Acetic acid (1% v/v) | 8.9 | 8.7 | 6.2 |

As shown in Table 1, the taxol solubilities decreased in supercritical $CO_2$ when combined with the cosolvents (1%, v/v), regardless of the types of the cosolvent, as compared to those in $CO_2$ only (it is noted that the taxol solubility of 13 μg/ml was obtained from the pure supercritical fluid extraction under a temperature of 80° C. and 350 bars of pressure). However, the taxol solubilities increased at least three times in cases where more than 5% (v/v) of the cosolvents other than water or the mixtures of water and the additional solvents were added to supercritical $CO_2$. In particular, methanol exhibits the better capability of enhancing the taxol solubility than ethanol and water. Also, when 10% (v/v) of methanol was used, the solubility was the highest, that is, 25 times more than solubility in pure $CO_2$. It believed that such an increase of taxol solubility by methanol is caused by the good ability of methanol to sufficiently dissolve taxol.

Further, the solubilities of taxol in a combined system of supercritical $CO_2$ and methanol increased proportionally with a volume ratio of methanol added. Likewise, ethanol also increased the solubility of taxol. Thus, based on the above results, alcoholic components were selected as major cosolvents in the present invention.

Water did not increase the taxol solubility proportionally with amounts of the added water. Rather, the solubility decreased as compared with the use of pure supercritical $CO_2$.

Example 2
The Effect of the Matrix of the Source Materials on Taxol Extraction and the Selection of Cosolvents:

In addition to the dissolving capacity of extraction solvents, the matrix environment in which taxol was located in nature is considered to influence the efficiency of taxol extraction. It is necessary to break interaction of taxol with the matrix of the source materials, if present. For this, suitable cosolvents can be employed in the extraction procedures. If taxol is released by such cosolvents from the matrix of source materials prior to extracting the source materials with supercritical $CO_2$, extraction efficiency can be improved.

Example 2 is directed to the selection of cosolvents suitable for avoiding the probable effects of the matrix against taxol extraction and for releasing taxol and its derivatives from the matrix.

To this end, a cellulose paper-taxol model was designed. If taxol does not interact with the cellulose paper, cosolvents may be selected only on the basis of its ability of dissolving taxol and its derivatives. If taxol interacts with the cellulose paper, however, cosolvent may be selected on the basis of its ability to break the interaction of taxol and the cellulose paper as well as its dissolving ability.

Taxol was absorbed into the cellulose paper and extracted with pure supercritical $CO_2$ or a combination of supercritical $CO_2$ and various cosolvents. The absorbing recovery of taxol was measured and is shown in Table 2 below.

The effect of the matrix of yew trees on extraction efficiency of taxol in supercritical fluid was investigated. First, 1 g of filter paper disc (Advantec No. 2, Toyo Roshi Kaisha, Tokyo, Japan) was cut into 1.0 cm in size, and put in a beaker. Then, a given amount of a solution of taxol in methanol (0.2 mg/ml) was added to the beaker and dried in vacuum oven for 24 hrs to use in the experiments. The condition of extraction was the temperature of 80° C. and 350 bars of pressure. Further, the flow rate of supercritical $CO_2$ was 40 kg/hr, and the temperature of the restrictor 50 was 160° C. Methanol, ethanol or water was used in 1–10% by volume as cosolvents. In addition, cosolvent mixtures including water-methanol or water-ethanol in ratios of 2:8, 5:5 and 8:2 (v/v), respectively, were prepared and added to the supercritical $CO_2$ by 20% by volume to use in the experiment.

According to the above method, the percent absorbing recovery (%) of taxol for pure $CO_2$ was measured to 0.46% by weight.

The term "percent absorbing recovery" refers to weight fractions of taxol obtained from supercritical extraction based on the weight of taxol absorbed on a filter paper disc. For example, if 1 mg of taxol is absorbed on a filter paper disc and the weight of the extracted taxol is 0.5 mg, then the percent absorbing recovery is 50%.

TABLE 2

% Absorbing recovery of taxol absorbed on cellulose paper based on various addition ratios of methanol, ethanol and water to supercritical $CO_2$ under a temperature of 80° C., pressure of 350 bars.

| Cosolvent | Addition ratio of cosolvent | | |
|---|---|---|---|
| | 1% | 5% | 10% |
| Methanol | 2.0% | 12.3% | 17.0% |
| Ethanol | 3.5% | 10.7% | 15.3% |
| Water | 5.2% | 64.0% | 81.0% |

*% Absorbing recovery = (weight of taxol absorbed on the cellulose paper/weight of taxol obtained by extraction) × 100

As shown in Table 2, water was most effective for releasing taxol from the cellulose paper. Generally, it is known that water is not suitable to use as a cosolvent in supercritical fluid extraction. However, the data in Table 2 indicated that water can provide benefits as a cosolvent with regard to interaction of taxol and the surrounding matrix despite its poor ability to dissolve taxol.

Example 3
Percent Extraction Recovery (%) of Taxol using Pure Supercritical $CO_2$:

Pure supercritical $CO_2$ extraction (i.e., without any cosolvents) of taxol from *T. cuspidate* was compared to the methanol extraction described in the above Comparative Example. Supercritical $CO_2$ extraction was performed at 80° C. and 350 bars of pressure to measure taxol yields. It was found that 0.024% (0.24 mg/g) of taxol existed in leaves, 0.0047% (0.13 mg/g) in stems and 0.0022% (0.022 mg/g) in roots.

The above results were compared to those in the above Comparative Example and shown as % extraction recovery (that is, the weight of taxol obtained with supercritical $CO_2$ per 1 g of taxol obtained with methanol extraction)×100) in Table 3 below. For example, if 1 mg of taxol was obtained with methanol extraction and the weight of the extracted taxol was 0.5 mg, then the %absorbing recovery is 50%.

TABLE 3

% Extraction recovery of taxol by pure supercritical $CO_2$ extraction as compared to methanol extraction under a temperature of 80° C. and the pressure of 350 bars from various parts of *T. cuspidate*.

| *T. cuspidate* | Leaves | Bark of stems | Roots |
|---|---|---|---|
| % Extraction recovery | 62.0% | 36.3% | 12.1% |

*% Extraction recovery = (weight of taxol obtained by supercritical $CO_2$ extraction/weight of taxol obtained by methanol extraction) × 100

As shown in Table 3, the recovery by pure supercritical $CO_2$ extraction is lower than that by methanol extraction of the Comparative Example.

Example 4
Percent Extraction Recovery from Source Materials using a Combination of Supercritical $CO_2$-cosolvent:

One can deduce from the results and findings of Examples 1 to 3 that the use of a cosolvent may enhance taxol yields and percent extraction recovery (%) in the supercritical fluid extraction process in comparison with the conventional organic solvent extraction and the pure supercritical fluid extraction.

In Example 4, extraction efficiency of taxol in supercritical $CO_2$ with methanol, ethanol and water as a cosolvent was measured and expressed in %extraction recovery. The obtained data are shown in Table 4 below.

TABLE 4

The % Extraction recovery of taxol in various supercritical $CO_2$ extractions where methanol, ethanol and water were used as cosolvents under a temperature of 80° C., 350 bars of pressure

| Cosolvent | | Addition ratio of cosolvent | | |
|---|---|---|---|---|
| | | 1% | 5% | 10% |
| Leaves | Methanol | 51% | 98% | 143% |
| of *T. cuspidate.* | Ethanol | 110% | 102% | 128% |
| | Water | 72% | 73% | 107% |
| Bark of stems | Methanol | 68% | 71% | 126% |
| of *T. cuspidate.* | Ethanol | 56% | 60% | 113% |
| | Water | 28% | 91% | 102% |
| Roots | Methanol | 65% | 61% | 68% |
| of *T. cuspidate.* | Ethanol | 71% | 66% | 100% |
| | Water | 16% | 52% | 64% |

*% Extraction recovery = (weight of taxol obtained by supercritical extraction/weight of taxol obtained by methanol extraction) × 100

In the extraction of the leaves, each cosolvent was added in 10% by volume and the %extraction recovery of taxol increased by 143% as compared to the conventional methanol extraction indicated in Example 2 above. In particular, ethanol added in 1% by volume increased the %extraction recovery by 110%. It should be noted that all of the cosolvents greatly enhanced the %extraction recovery of taxol in these experiments whereas the cellulose paper-taxol model experiment of Example 2 above shows that no cosolvent exhibits 40% or more of an increase in the %extraction recovery, with the exception of water. In this regard, note that the term "% extraction recovery" is related to "% absorbing recovery" in Example 2. Therefore, it is believed that the taxol is absorbed to the surrounding matrix in yew trees but not absorbed as strongly as to cellulose paper in Example 2. Thus, the extraction efficiency may be greatly improved by solvents containing OH group, which may have a stronger leaving force as compared to supercritical $CO_2$.

In Table 4 above, the value of 100% or more in the % extraction recovery means that taxol has not been thoroughly extracted from the yew trees by conventional methanol extraction.

The %extraction recovery in the barks of stems was measured to be above 100% in the experiments where 10% methanol, ethanol or water was added. Although the supercritical fluid extraction efficiency was less effective in the roots than in the leaves and the bark, the %extraction recovery with 10% ethanol added was 100%.

In cases where water was used as a cosolvent, the addition of 5% or 10% water significantly increased the recovery as when compared to that in pure supercritical $CO_2$ of Example 3, whereas the addition of 1% water rather decreased it. As explained in Example 3, this was apparently due because water does not increase taxol solubility in a supercritical fluid, but plays a role in accelerating the release of taxol from the surrounding matrix to improve taxol extraction yields. This can provide some explanation as to why the addition of a smaller amount of water (i.e., 1%) could not increase the recovery. Namely, a small amount of water can neither increase the solubility of taxol nor affect on the release of taxol from the matrix of the source materials.

Example 5
Extraction Selectivity and Percent Extraction Selectivity of Taxol by Supercritical $CO_2$-cosolvent Extraction:

In the example, the extraction selectivity of taxol against other impurities was measured using conventional methanol extraction and the supercritical fluid-cosolvent extraction of the present invention. Also, the percent extraction selectivity was determined based on the obtained extraction selectivity of taxol.

The term "extracts" refers to all components extracted from the source materials including taxol. It is preferable if taxol may be selectively extracted without other impurities since subsequent isolation and purification steps are directly influenced by a content of taxol in the obtained extracts.

The term "extraction selectivity" is defined as the weight of taxol, which is finally obtained upon completion of all procedures, divided by the total weight of the extracts. A higher extraction selectivity indicates a higher content rate of taxol in the extracts obtained from the extracting process.

The term "%extraction selectivity" in the invention is defined as follows:

%extraction selectivity=(extraction selectivity of supercritical fluid extraction)/(extraction selectivity of conventional methanol extraction)×100

In this example, the extraction selectivities were determined in a part of *T. cuspidate* having the best extraction yields, i.e., the leaves, as shown in the results of Example 4. The obtained %extraction selectivity was compared to that of methanol extraction of the Comparative Example. The results are shown in Table 5 below.

TABLE 5

Extraction selectivity and % extraction selectivity of extracts from leaves of *T. cuspidate* in supercritical $CO_2$ -cosolvent extractions under a temperature of 80° C. and the pressure of 350 bars

| | Conventional Methanol Extraction | Supercritical $CO_2$-Cosolvent Extraction Added Cosolvent | | |
|---|---|---|---|---|
| | | Methanol (10%) | Ethanol (10%) | Water (10%) |
| extraction selectivity | 0.11% | 0.42% | 0.61% | 0.62% |
| % extraction selectivity | 100% | 381% | 555% | 564% |

As shown in Table 4, when methanol, ethanol or water was added to supercritical $CO_2$, in 10% by volume, the %extraction selectivity of taxol in the leaves was increased by 400–600%. These data indicated that, in accordance with the invention, the amounts of separated taxol are linearly increased by about 4–6 times than those in methanol extraction.

Example 6
The Cosolvent Component Ratio for Establishing the Condition of Supercritical Extraction:

In the example, when water and alcohol were used as cosolvents, yields of supercritical fluid extraction were determined and the results are shown in Table 6 below.

TABLE 6

Taxol yields extracted depending on various compositions of cosolvents in the leaves of *T. cuspidate* (80° C., 350 bars)

| Extraction Method Methanol Extraction Supercritical fluid extraction: Composition of cosolvent (%, v/v) | | | | Yields of extracted Taxol |
|---|---|---|---|---|
| $CO_2$ | Methanol | Ethanol | Water | 200 µg/g |
| 100 | — | — | — | 54 µg/g |
| 90 | 10 | — | — | 72 µg/g |
| 80 | 20 | — | — | 189 µg/g |
| 90 | — | — | 10 | 25 µg/g |
| 80 | — | — | 20 | 98 µg/g |
| 90 | — | 10 | — | 119 µg/g |
| 80 | — | 20 | — | 158 µg/g |
| 90 | 5 | — | 5 | 208 µg/g |
| 80 | 10 | — | 10 | 203 µg/g |
| 90 | — | 5 | 5 | 242 µg/g |
| 80 | — | 10 | 10 | 336 µg/g |

As shown in Table 6, the extraction efficiency was more enhanced by methanol, ethanol or water than by combinations of water and methanol or ethanol (1:1 v/v). Particularly, when the cosolvent mixture comprising water and ethanol in 1:1 by volume was added to $CO_2$ in 20% by volume, contents of taxol extracted increased by 150% or more, as compared to the methanol extraction.

Example 7
The Effect of the Compositional Ratio of Water and Alcohol on Extraction Yields by Supercritical Fluid Extraction:

When a mixture of water and alcohol was used as a cosolvent, the correlation of a compositional ratio of water and alcohol with extraction yields were investigated in order to determine the optimal ratio. Methanol or ethanol was used in this experiment as an alcohol.

Figure 3:
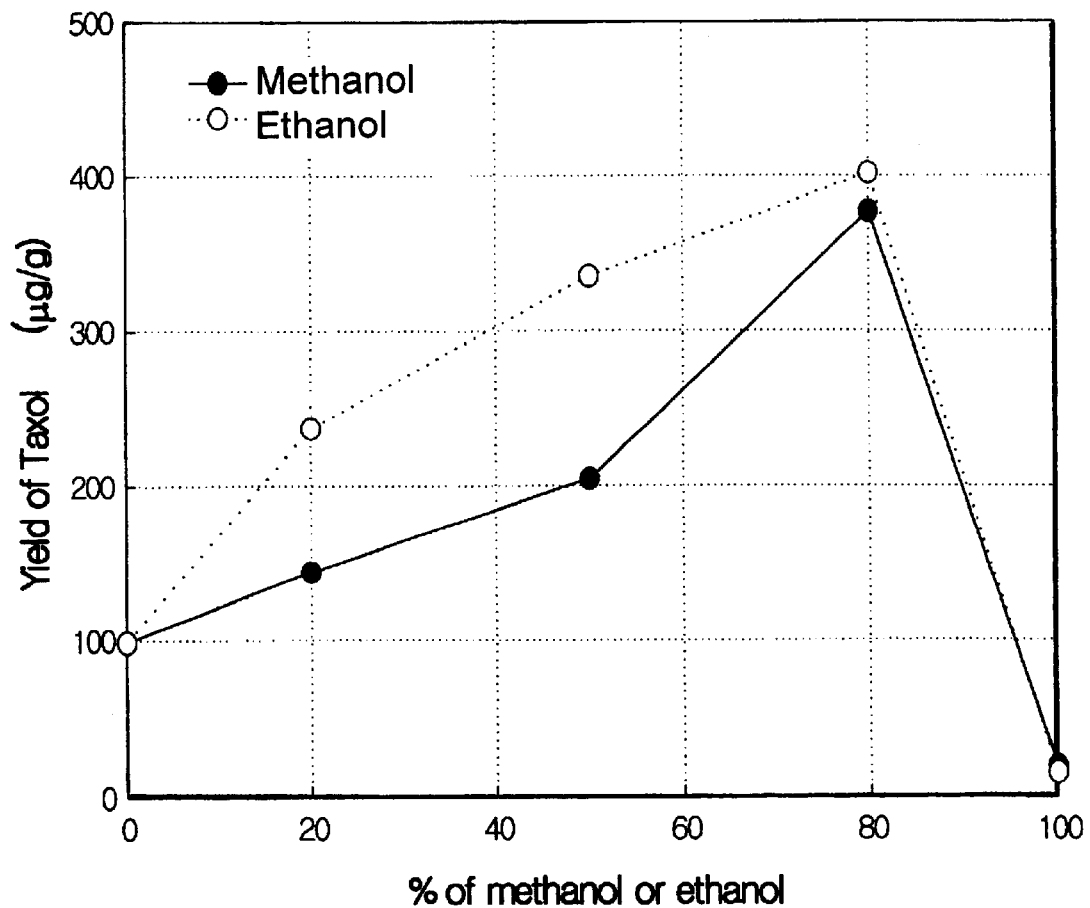
FIG. 3 is a graph that illustrates taxol yields extracted from yew leaves. Taxol yields depended on a compositional ratio of the cosolvent mixture of water-methanol or water-ethanol.

The mixed ratios of water and methanol or ethanol were increased from 2:8 to 8:2 and each mixed cosolvent was added to supercritical $CO_2$ in 20% by volume. The change in taxol yields was then measured. The results are shown in FIG. 3. As shown in FIG. 3, when the mixture of water:alcohol in a 2:8 ratio was added to supercritical $CO_2$ in 20% by volume, the highest yield of extraction was obtained.

Figure 4:
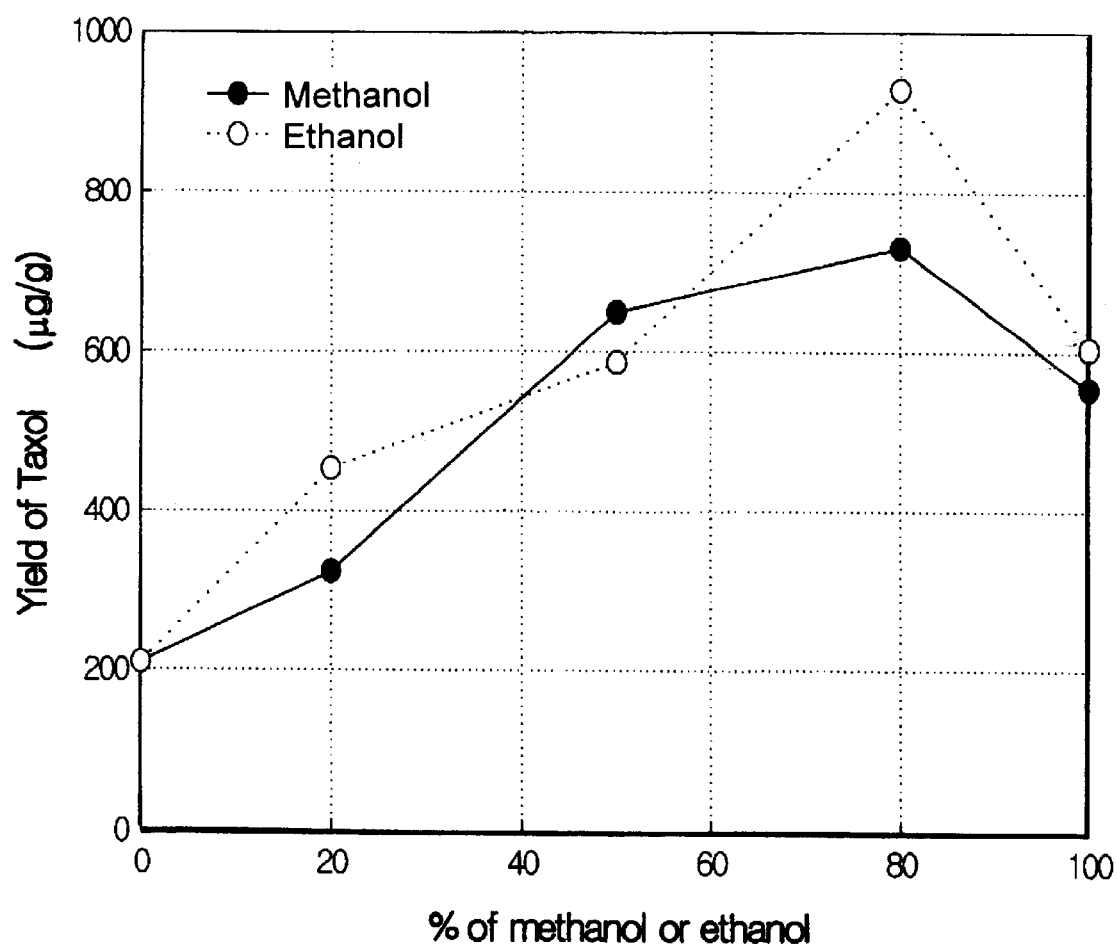
FIG. 4 is a graph that illustrates taxol yields extracted from yew leaves. Taxol yields depended on a compositional ratio of the cosolvent mixture of water-methanol or water-ethanol.

The source materials were the leaves of *T. cuspidate*, taken in October 1999. In another experiment similar to that described above was carried out with the leaves taken in August 1998. Likewise, the cosolvent mixture of water:alcohol in a 2:8 volume ratio provided the highest yield. The results are shown in FIG. 4.

Example 8
Extraction of Taxol using a Supercritical Extraction Process:

Taxol was extracted with the supercritical fluid extraction of the present invention. The extraction conditions were determined as follows: supercritical $CO_2$-ethanol-water= 80:16:4; a flow rate of 40–80 kg/hr of the supercritical fluid; a temperature of 80° C. and 350 bars of pressure. This condition was set up on the basis of the results of Examples 1 to 7 above. Samples for the determination of the yields were taken at 20 minutes intervals for a total 6 hours.

Figure 5:
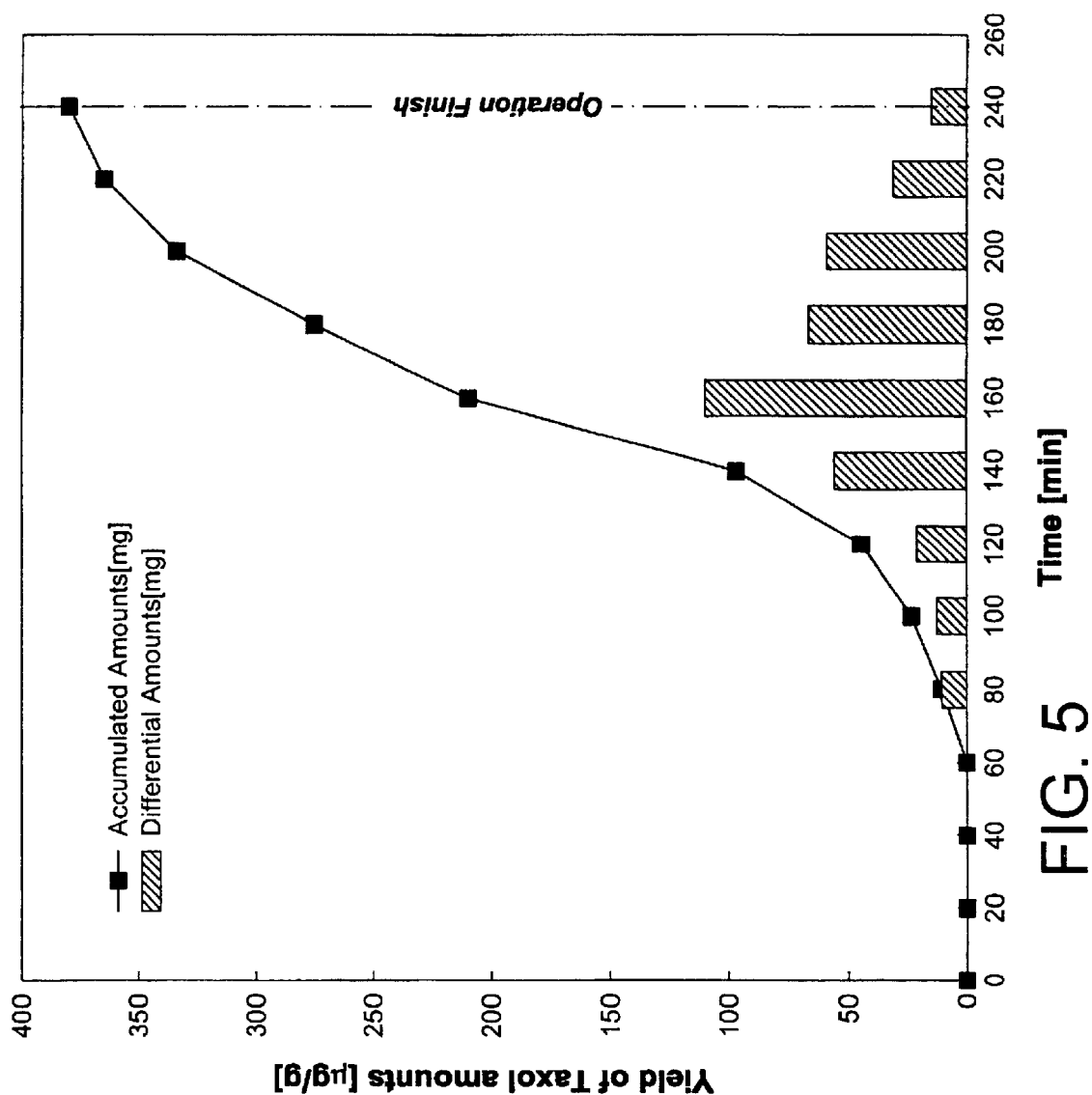
FIG. 5 is a graph that illustrates taxol extraction yields from an experiment where the supercritical fluid and cosolvent used were a mixture of supercritical carbon dioxide:ethanol:water (80:16:4 in volume ratio) and where the extraction was performed under conditions in which there was a temperature of 80° C., a pressure of 350 bars, and a flow rate of 40 kg/hr of the supercritical fluid. *T. cuspidate* was used as source material.
Figure 6:
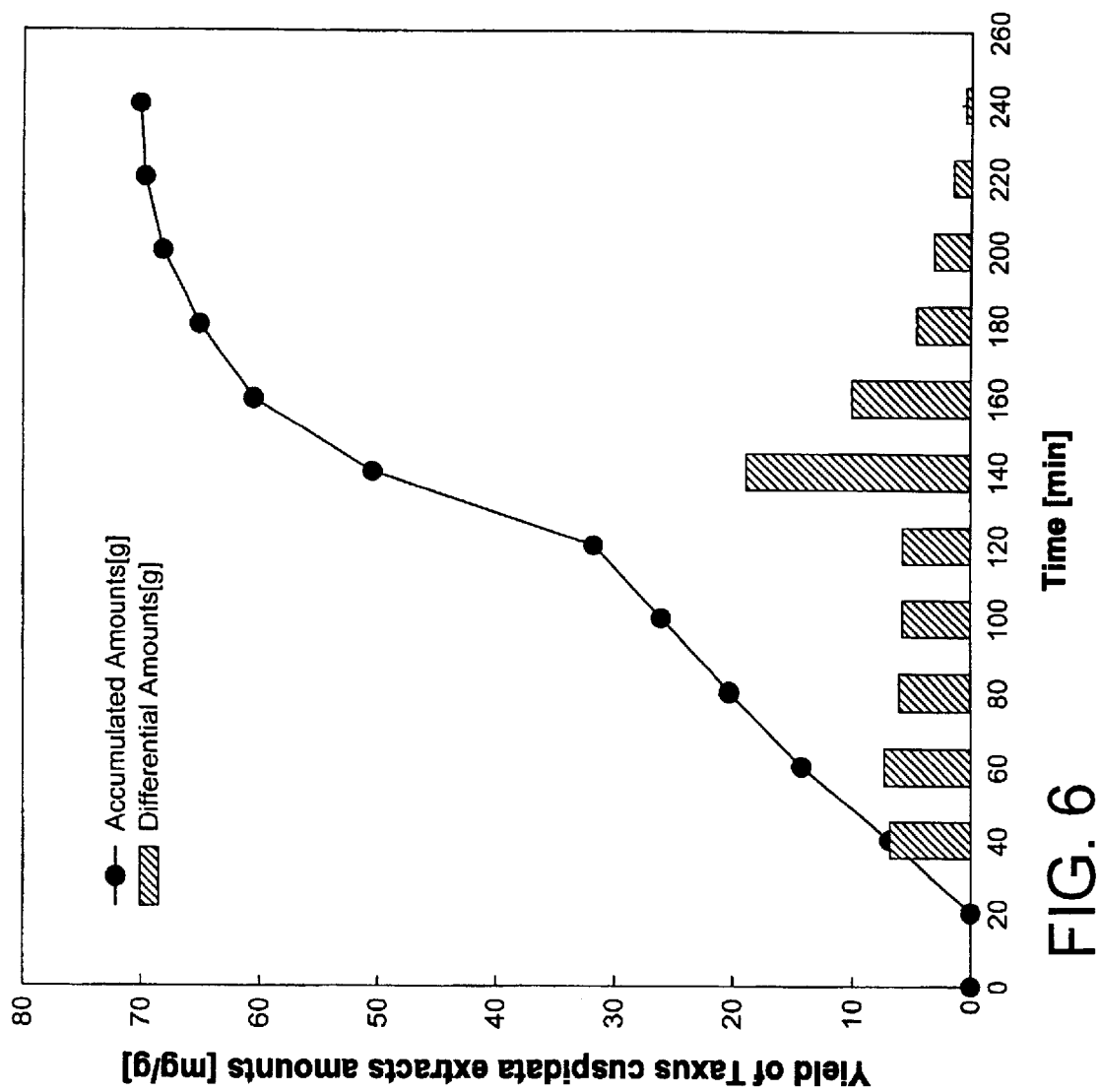
FIG. 6 is a graph that illustrates extracts yield from an experiment where a supercritical fluid and cosolvent used were a mixture of supercritical carbon dioxide:ethanol:water (80:16:4 v/v/v). The experiment was conducted under conditions in which there was a temperature of 80° C., pressure of 350 bars, and a flow rate of 40 kg/hr of the supercritical fluid. *T. cuspidate* was used as a source material.

Taxol yields and yields of extracts are shown in FIGS. 5 and 6, respectively. As shown in FIGS. 5 and 6, taxol was not extracted for 1 hr. from the starting time of the extraction process. This is because sufficient contact of the cosolvents with the source materials requires a certain period as well as it takes some time for the supercritical $CO_2$ and the cosolvents to pass through the extractor. For example, if the supercritical fluid passes through the extractor at a flow rate of 40 kg/hr, it takes about 10 minutes for the cosolvents to pass from the bottom to the top of the extractor. Furthermore, the flow of the supercritical fluid is also affected by its angle. The movement of the fluid may be hindered by any obstacle placed perpendicularly to its direction.

Example 9
Increase of Extraction Selectivity of Supercritical Fluid Extracts by Liquid-liquid Separation:

In the Example, hexane was used in the liquid—liquid separation of the extracts obtained from supercritical fluid extraction. The taxol content was 0.55% in the extracts before the liquid—liquid separation and increased to 0.82% after the liquid—liquid separation. This indicates that 33% of impurities other than taxol could be removed by the liquid—liquid separation using hexane.

Example 10
HPLC Analysis of Methanol Extracts and Supercritical Fluid Extracts:

The extracts subjected to the liquid—liquid separation in Example 9 were analyzed by HPLC to measure a content of taxol and its derivatives. The results are shown in FIG. 7 along with the results of the methanol extracts.

As shown in FIG. 7, each peak indicates ① taxol peak, ② cephalomanin, ③ Vaccatin III, and ④ 10-diacetylvacatin III. Identification of peaks was carried out with a co-injection method using the extracts and a standard sample in a mixture, each being the same amount.

Figure 7A:
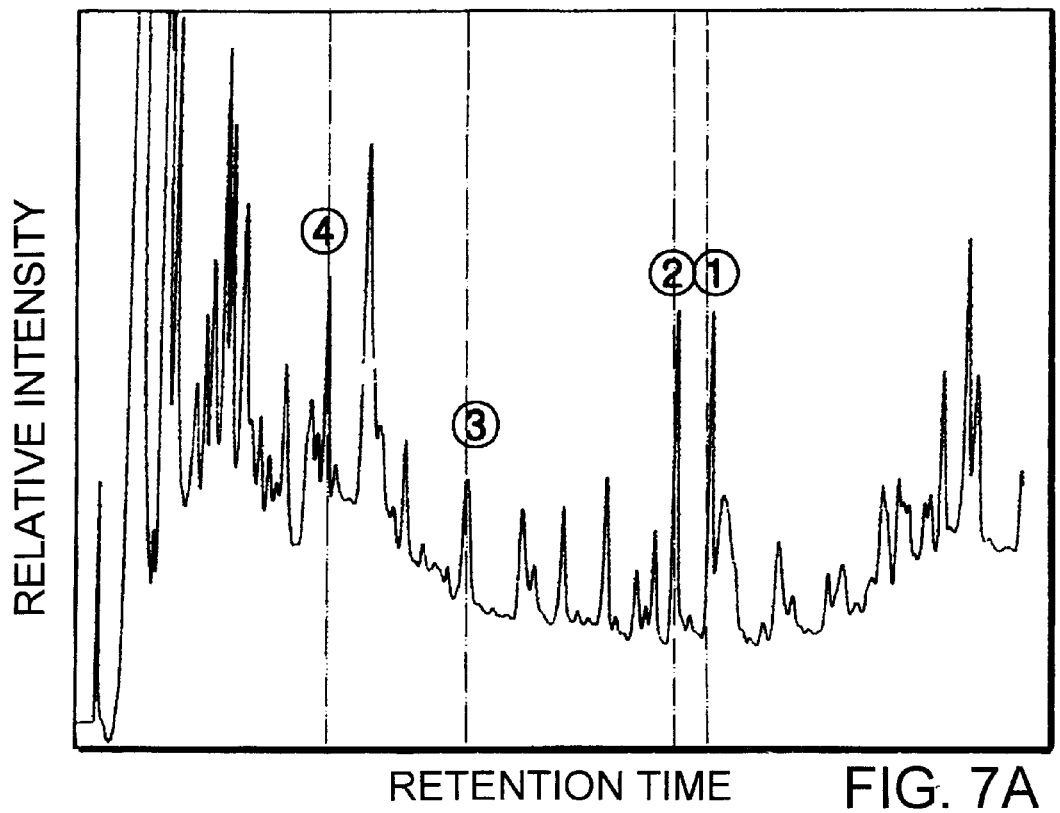
FIG. 7 is a HPLC chromatogram of taxol extracts from yew leaves.
Figure 7B:
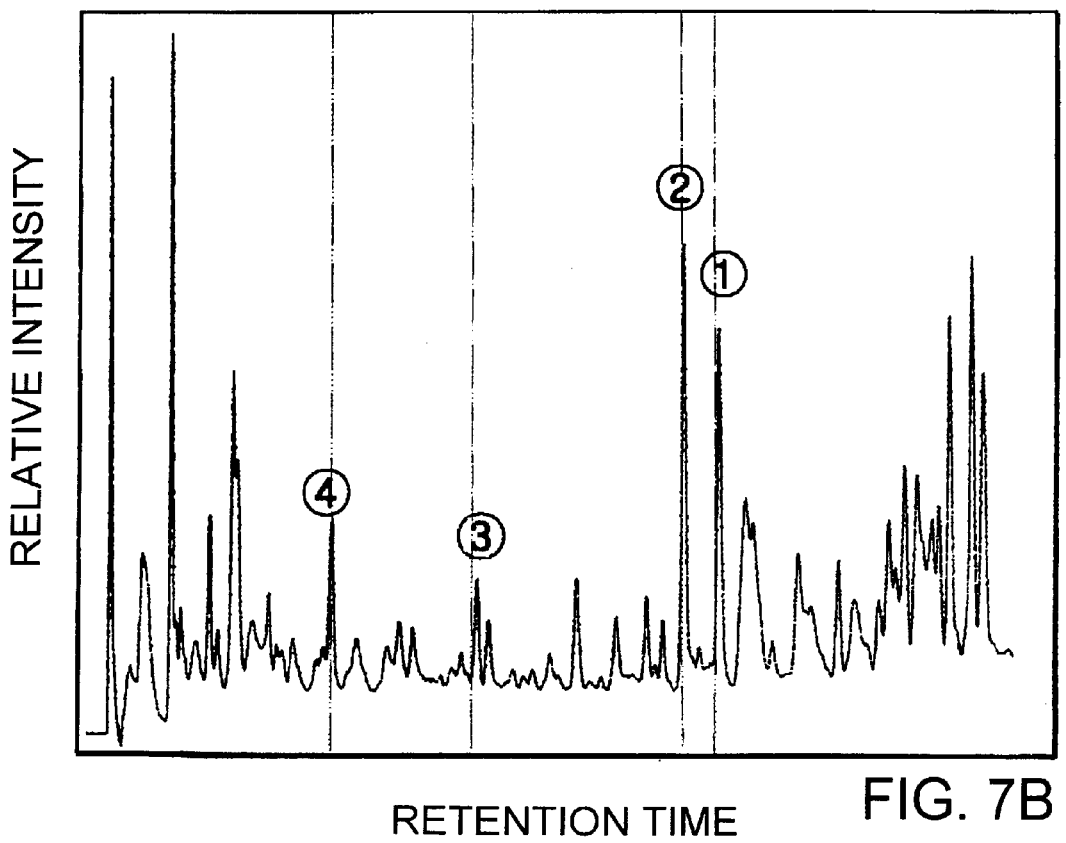
Figure 8A:
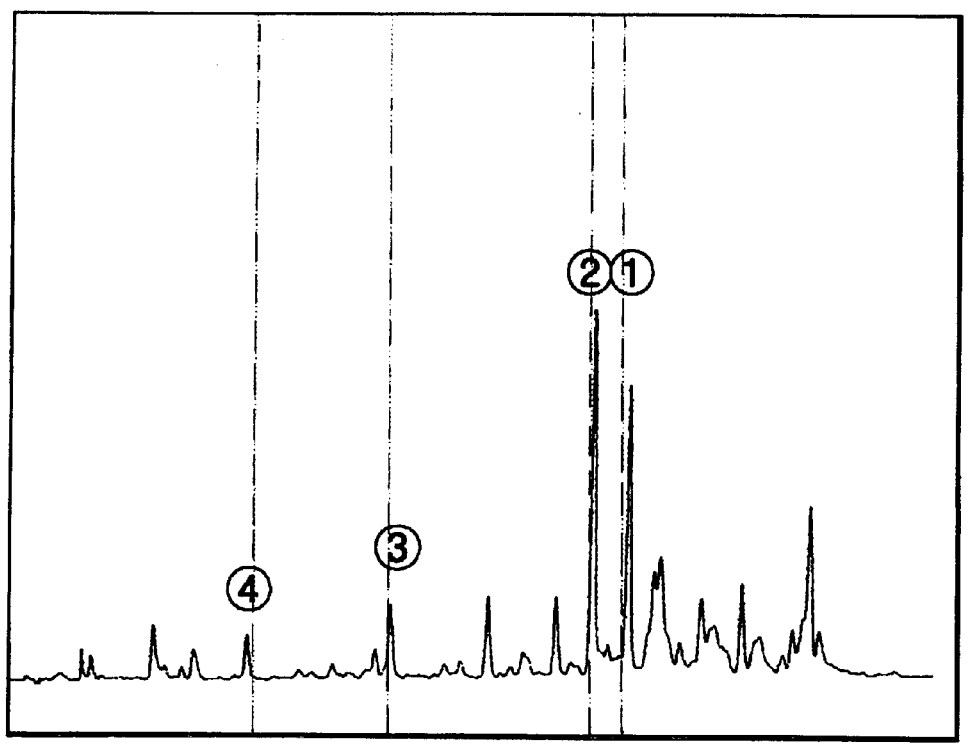
FIG. 8 shows HPLC analysis of extracts subjected to supercritical fluid extraction and column purification.
Figure 8B:
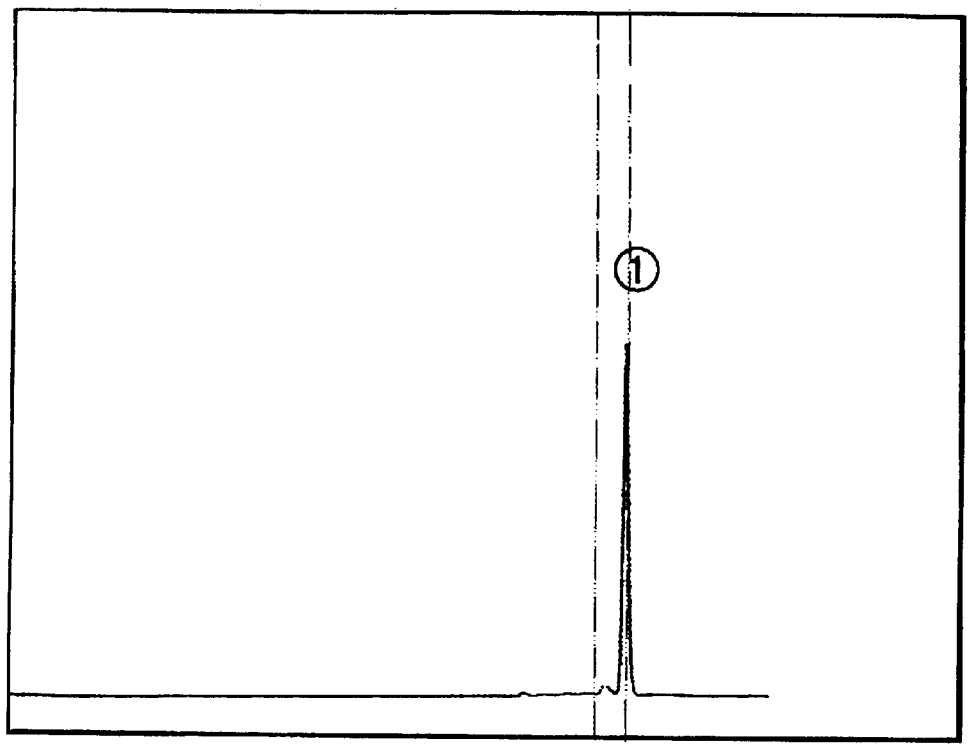

As seen in FIGS. 7 and 8, the methanol extracts (FIG. 7*a*) produced a number of impurities peaks, which must be removed as compared to the supercritical fluid extracts (FIG. 7*b*) in the early stage of retention time. This shows that separating and purifying steps become simpler in accordance with the present invention.

Example 11
Preparation of Taxol and its Derivatives using Chromatography:

In this Example, taxol with high purity was prepared from the extracts of Example 9 by column chromatography.

First, the extracts were subjected to silica gel chromatography. As a result, the taxol content in the extracts increased to 1.58%. Silica gel can be reusable after washing with methanol and chloroform. Peaks of tactic acids were removed in the first purification step.

Subsequently, the purified products were subjected to the second purification step using RP-18 resin. Taxol contents increased to 15% in the extracts as demonstrated by HPLC analysis. The results of the HPLC analysis were shown in FIG. 8*a*. RP-18 resin can be reusable after eluting non-polar materials with isopropyl alcohol and washing with methanol.

The second purified products were again subjected to the third purification step using silica gel column. As a result, the taxol content increased to 43% in the extracts, and peak of vaccatin III disappeared as shown from the HPLC analysis. Thus, vaccatin III may be obtained from this step. Silica gel can be reusable by the same procedure as the first purification step.

The third purified products were subjected to the fourth purification step using LH-20 filler. As a result, the taxol content increased to 84%, and cephaloman, which has a similar retention time to taxol, was removed.

Finally, the fourth purified products were subject to the fifth column purification using RFP HPLC column (Phenomenex Co.). The purified products were recrystallized with water:methanol (1:1, v/v) to give taxol with purity of 99%. HPLC analysis of taxol obtained was shown in FIG. 8*b*.

As explained above, according to the present invention, taxol with high purity can be prepared and fractions of taxol derivatives were obtained.

What is claimed is:

1. A method for isolating Taxol or derivatives thereof from a source material, said method comprising:
    (a) extracting said source material with a supercritical fluid and a cosolvent to obtain an extract;
    (b) liquid—liquid separating said extract with an organic solvent to obtain a solvent layer; and
    (c) isolating Taxol or said derivatives thereof from said solvent layer by column chromatography.

2. The method of claim 1, wherein said supercritical fluid is supercritical carbon dioxide.

3. The method of claim 1, wherein the ratio of said supercritical fluid to said cosolvent is between 75:25 and 85:15.

4. The method of claim 1, wherein said cosolvent is a mixture of water and at least one alcohol.

5. The method of claim 4, wherein said at least one alcohol is methanol or ethanol.

6. The method of claim 4, wherein the volumetric ratio of water to said at least one alcohol is between 30:70 and 5:95.

7. The method of claim 6, wherein the volumetric ratio is 20:80.

8. The method of claim 1, wherein said supercritical fluid extracting step is performed at a temperature of 60 to 100° C. and a pressure of 300 to 400 bars.

9. The method of claim 8, wherein said temperature is 80° C. and said pressure is 350 bars.

10. The method of claim 1, wherein said supercritical fluid extracting step is performed at a temperature of 75 to 85° C., a pressure of 330 to 370 bars, and a flow rate of 30–50 kg/hr of said supercritical fluid.

11. The method of claim 1, wherein said organic solvent comprises n-hexane.

12. The method of claim 11, wherein the volumetric ratio of n-hexane to said cosolvent is 1:1 and said liquid—liquid separating step is performed from one to three times.

13. The method of claim 1, wherein said extracting and said liquid—liquid separating steps are performed continuously or non-continuously.

14. The method of claim 1, wherein column chromatography comprises using multiple columns to isolate Taxol or said derivatives, wherein each of said multiple columns comprises a column resin.

15. The method of claim 14, wherein column chromatography is performed continuously or non-continuously.

16. The method of claim 14, wherein said column resins comprise silica gel, RP-18, or Sephadex column resins.

17. The method of claim 16, wherein an amount of said silica gel resin is 10 times the weight of an extract applied to said column and a stepwise gradient system of chloroform:methanol is used as an eluant.

18. The method of claim 17, wherein taxol and said derivatives are eluted from said silica gel resin.

19. The method of claim 16, wherein an amount of said RP-18 resin is 10 times the weight of an extract applied to said column, and methanol is used as an eluant.

20. The method of claim 19, wherein baccatin III is eluted from said RP-18 resin.

21. The method of claim 16, wherein an amount of said silica gel resin is 33 times the weight of an extract applied to said column, and wherein a solution of dichloromethane:methanol is used as eluant.

22. The method of claim 16, wherein an amount of said Sephadex resin is 65 times the weight of an extract applied to said column, and wherein methanol is used as eluant.

23. The method of claim 22, wherein cephalomannine is eluted from said Sephadex resin.

24. The method of claim 14, wherein a column comprising a pentafluorophenyl resin is the final column of said multiple columns.

25. The method of claim 24, wherein the amount of said pentafluorophenyl resin used is 133 times the weight of an extract applied to said column, and wherein an acetonitrile:water gradient system is used as eluant.

26. The method of claim 25, wherein the acetonitrile content is changed from 60% to to 90%.

27. The method of claim 1, said method further comprising recrystallizing said isolated taxol or derivatives thereof.

28. An apparatus for isolating Taxol or derivatives thereof from source materials, said apparatus comprising a reservoir for supercritical fluid, an extractor into which the source material is fed to from an extract mixture, a separating vessel that separates the supercritical fluid from the extract mixture, a source of organic solvent, a liquid—liquid separator operable to separate the extract mixture with the organic solvent to obtain a solvent layer, and at least one column for column chromatography in communication with the solvent layer, all being placed on-line.

29. The apparatus of claim 28, wherein said separating vessel separates the supercritical fluid from the extract mixtures in a continuous form.

30. The apparatus of claim 28, which is operable to allow recovery and recycling of all solvents used in the extractor, separating vessel and liquid—liquid separator, with the exception of any solvents transferred into the column chromatography.

* * * * *